United States Patent [19]

Smith

[11] Patent Number: 5,658,559
[45] Date of Patent: Aug. 19, 1997

[54] OCCLUSIVE/SEMI-OCCLUSIVE LOTION FOR TREATMENT OF A SKIN DISEASE OR DISORDER

[75] Inventor: James A. Smith, Chatham, Mass.

[73] Assignee: Creative Products Resource Associates, Ltd., North Caldwell, N.J.

[21] Appl. No.: 480,534

[22] Filed: Jun. 7, 1995

Related U.S. Application Data

[63] Continuation of Ser. No. 220,394, Mar. 30, 1994, abandoned, which is a continuation of Ser. No. 992,887, Dec. 16, 1992, abandoned.

[51] Int. Cl.$^6$ ................................................. A61K 9/107
[52] U.S. Cl. ........................... 424/78.02; 424/78.03; 424/401; 514/938
[58] Field of Search .................... 424/78.03, 78.02; 514/938

[56] References Cited

U.S. PATENT DOCUMENTS

| | | | |
|---|---|---|---|
| 2,999,265 | 9/1961 | Duane et al. | 424/401 |
| 3,608,070 | 9/1971 | Nouvel | 424/78.02 |
| 3,627,871 | 12/1971 | Groves | 514/887 |
| 3,928,261 | 12/1975 | Schertler | 524/405 |
| 4,017,615 | 4/1977 | Shastri et al. | 514/939 |
| 4,210,633 | 7/1980 | Takruri et al. | 424/78.05 |
| 4,275,222 | 6/1981 | Scala | 424/63 |
| 4,278,655 | 7/1981 | Elmi | 424/47 |
| 4,305,936 | 12/1981 | Klein | 514/174 |
| 4,497,794 | 2/1985 | Klein et al. | 514/859 |
| 4,559,157 | 12/1985 | Smith et al. | 428/320.2 |
| 4,608,392 | 8/1986 | Jacquet et al. | 514/844 |
| 4,690,821 | 9/1987 | Smith | 424/320.2 |
| 4,692,329 | 9/1987 | Klein et al. | 514/859 |
| 4,727,064 | 2/1988 | Pitha | 514/971 |
| 4,806,572 | 2/1989 | Kellett | 424/401 |
| 4,820,508 | 4/1989 | Wortzman | 424/59 |
| 4,992,478 | 2/1991 | Geria | 514/938 |
| 5,004,598 | 4/1991 | Lockhead et al. | 514/939 |
| 5,013,545 | 5/1991 | Blackman et al. | 514/887 |
| 5,174,995 | 12/1992 | Davis | 424/400 |
| 5,208,035 | 5/1993 | Okuyama et al. | 424/446 |
| 5,210,099 | 5/1993 | Mody et al. | 514/939 |
| 5,322,685 | 6/1994 | Nakagawa et al. | 424/78.03 |
| 5,422,361 | 6/1995 | Munayyer et al. | 514/938 |

OTHER PUBLICATIONS

Nadolsky et al., *Soap/Cosmetics/Chemical Specialties*, Apr. 1985, pp. 30–32.

C.E. Strattan, *Pharmaceutical Technology*, Jan. 1992, pp. 68–72.

*Primary Examiner*—Amy Hulina
*Attorney, Agent, or Firm*—Cushman Darby & Cushman IP Group of Pillsbury Madison & Sutro, LLP

[57] ABSTRACT

The present invention is an occlusive or semi-occlusive barrier moisturizing lotion useful for treating pathologies of the skin. The lotion is composed of an oil-in-water emulsion that includes water, one or more emollients, at least one polyhydric alcohol, a barrier polymer, and a therapeutical agent, preferably a dermatological agent such as a steroid. When the lotion is applied to the skin and dries, a polymeric film forms on the surface of the lotion to retain the therapeutic agent in contact with the surface of the skin. The emollient system of the lotion provides a moisturizing and soothing effect on the skin, and the occlusive/semi-occlusive nature of the lotion causes hydration of the skin to facilitate and enhance penetration of the drug into the skin.

2 Claims, No Drawings

OCCLUSIVE/SEMI-OCCLUSIVE LOTION FOR TREATMENT OF A SKIN DISEASE OR DISORDER

This is a continuation of application Ser. No. 08/220,394, filed on Mar. 30, 1994, entitled OCCLUSIVE/SEMI-OCCLUSIVE LOTION FOR TREATMENT OF A SKIN DISEASE OR DISORDER, which is a continuation of application Ser. No. 07/992,887, filed on Dec. 16, 1992, both abandoned.

BACKGROUND OF THE INVENTION

Topical medications that include corticosteroids are used for treating skin conditions such as atopic dermatitis, psoriasis and other pathologies of the skin. Current steroid-containing products are available mainly as gels, lotions or ointments that are supplied in tubes or bottles and applied to an affected area of the skin by hand.

To enhance the effect of asteroid agent on the skin, it is desirable to have a moisturizing or emollient effect to supplement the curative action of the steroid. Also, it is also preferred that an occlusive barrier be applied to the skin during application to enhance the retention and the bioavailability of the steroid.

Current dermatological treatments apply an appropriate amount of asteroid cream or ointment to the skin, and then cover the affected area with a piece of plastic film to provide a barrier to occlude the skin and facilitate the retention of moisture on-the skin surface. A commonly used film is composed of a polyvinylidene chloride (PVDC) copolymer and marketed under the trademark Saran®. This way of occluding the surface of the skin, however, is difficult to administer and inconvenient to the patient.

Therefore, it is an object of the present invention to provide a moisturizing lotion for administering a therapeutic agent to the skin while simultaneously forming an occlusive or semi-occlusive barrier on the surface of the skin. Another object is to provide a lotion that will provide enhanced penetration of a therapeutic agent into the skin and a high level of moisturizing activity. Yet another object is to provide a lotion that will adhere to a moist skin surface and provide an occlusive/semi-occlusive barrier.

SUMMARY OF THE INVENTION

The present invention is an occlusive or semi-occlusive barrier moisturizing lotion useful for treating pathologies of the skin. The lotion is composed of an oil-in-water emulsion that includes water, one or more emollient, at least one polyhydric alcohol, a barrier polymer, and a therapeutic agent, preferably asteroid such as a corticosteroid. Optionally, the lotion may include a penetration enhancing agent, surfactants, preservatives and fragrance.

When the lotion is applied to an affected area of the skin, a relatively uniform application of the occlusive/semi-occlusive lotion is delivered onto the skin surface. As the lotion dries, a polymeric film forms on the surface of the lotion which retains the therapeutic agent in place and in intimate contact with the surface of the skin. The occlusive/semi-occlusive nature of the present lotions also prevents water evaporation so that the skin becomes hydrated and facilitates the penetration of the drug into the skin. The lotions may also be applied to a moist skin surface, as for example, after showering or bathing when the skin is fully hydrated.

The lotions may be applied to the skin by hand or by means of an absorbent fibrous or cellular sheet material that is impregnated with the composition. When the impregnated sheet is pressed or rubbed against a skin surface, an effective amount of the composition is released and coated onto the skin without skipping or separating on the skin.

DETAILED DESCRIPTION OF THE INVENTION

The invention provides an occlusive or semi-occlusive moisturizing lotion for use in the treatment of skin disorders and maladies such as atopic dermatitis, psoriasis, and the like. The lotion is an oil-in-water emulsion that comprises one or more emollient, water, at least one barrier polymer, and a bioactive therapeutic agent, which is emulsified to provide a finished composition that has a lotion-consistency. Preferably, the lotion further comprises a polyhydric alcohol, a penetration enhancing agent, one or more surfactants, preservatives and fragrance.

Emollients. The lotion will incorporate an effective amount of one or more emollients, that are preferably present in an amount equal to about 0.5–20 wt-% of the entire lotion. As used herein, the term emollient is meant to include any of the inorganic or organic oils and/or waxes that generally function to lubricate the skin surface and to prevent evaporative loss of skin moisture supplied by underlying tissues. Emollients also function to provide a protective barrier against environmental irritants.

Emollient oils useful in the practice of the present invention include those commonly employed in emollient creams and lotions, such as liquid hydrocarbons (petrolatum, mineral oil, and the like), vegetable and animal fats and oils (lanolin and its derivatives, cholesterol and its derivatives, phytosterols, and the like), alkyl fatty acid esters (methyl, isopropyl, and butyl esters of fatty acids, and the like), fatty alcohol esters of benzoic acids and $C_4$–$C_6$ alkanoic acids, phospholipids and their derivatives (lecithin, cephalin and the like), and silicones.

The lotions preferably includes a minor amount, about 0.5–8 wt-%, of a phytosterol, a polyoxyethoxylated soyasterol formed by derivatizing the $C_3$—OH group of phytosterol or campersterol with 5–25 ethanoloxy groups. For example, a polyethoxylated soya sterol from the Generol® 122 series (Generol 122E-25, Generol 122E-10 and Generol 122 (mix)) that is commercially available from Henkel Corporation, Ambler, Pa., may be used. Preferably about 0.75–3 wt-% of a polyoxyethylene-10-16-soya sterol (General 122E-10 or General 122E-16) will be included in the oil phase component of the present lotions.

A preferred class of emollient oils for the present lotions is the fatty alcohol esters of benzoic acid such as the $C_{12}$–$C_{15}$ alkylbenzoates, available commercially as Finsolv TN (described in U.S. Pat. Nos. 4,278,655 and 4,275,222), Finsolv P, Finsolv BOD, and Finsolv SB) (Finetex, Inc.). Preferably, the emollient component of the lotion will comprise about 0.5–15 wt-% Finsolv TN.

The emollient portion of the lotion may also comprise a minor amount of silicone oil or mineral oil, preferably about 0.5–18 wt-%, more preferably about 1–5 wt-%, which acts as a barrier against skin irritants, and controls the foaming caused by any added surfactants or ionic antimicrobial agents. Mineral oils are preferred and may consist of one or more of the commercially available white mineral oils such as Carnation® White Mineral Oil available from Witco Chemical Corp., Petrolia, Pa. (Viscosity at 40° C.:10.8–13.6 cst, S.G. at 25° C.:0.829–0.845).

The present lotions may also include an amount of a polyalkylene glycol ether of a $C_{12}$–$C_{18}$ fatty alcohol, such as cetereth-20 (a polyethylene glycol ether of cetearyl alcohol) or laureth-23 (a polyethylene glycol lauryl ether). Also useful are the $C_{12}$–$C_{18}$ fatty acid-$C_2$–$C_5$ polyol esters such as glyceryl monostearate, ethylene glycol monostearate and polyethylene glycol distearate.

Another useful class of emollient oil is the $C_6$–$C_{12}$-acid diesters of propylene glycol, such as propylene glycol dicaprylate, propylene glycol dicaprate, mixtures thereof or the mixed caprate, caprylate ester. A preferred mixed ester is propylene glycol dicaprylate-dicaprate, available as Standamul 302 (Henkel Corp., Ambler, Pa.).

A further useful class of emollient oils are the mixed fatty acid-fatty alcohol esteralkoxylates of polyoxyethylene glycol wherein the acid and alcohol components each comprise 12–18 carbon atoms and the polyoxethylene glycol component is made up of 2–5 ethylenoxy units. A preferred emollient of this class is polyoxyethylene myristyl ether myristate (Standamul 1414, Henkel Corp., Ambler, Pa.).

Other emollient oils that are useful in the present lotions include benzyl alcohol esters of one or more $C_{10}$–$C_{20}$ fatty acids, such as benzyl linoleate (Dermol 618, Alzo, Inc., Matawan, N.J.); liquid fatty alcohol esters of $C_3$–$C_6$ aliphatic carboxylic acids such as isodecyl neopentanoate (Dermol 105, Alzo, Inc., Matawan, N.J.); $C_{12}$–$C_{18}$ fatty alcohol esters of $C_4$–$C_6$ alkanoic acids such as isostearyl neopentanoate (Ceratophyll® 375, Van Dyk and Co., Belleville, N.J.); waxy $C_2$–$C_5$ alkyl esters of fatty acids such as isopropyl myristate (Credocol IPM, Croda, Inc.); and alkanol di- or tri-esters of dimer or trimer acid of oleic acid such as triisopropyl trimerate (Schercemol TT, Scher Chemicals, Clifton, N.J.) and diisopropyl dimerate (Schercemol DID). Also useful are polyoxyalkoxylated emollients, as for example, polyoxylated lanolins such as PPG-12-PEG-50 (Lanexol AWS).

It is preferred that the emollient portion of the lotion is about 0.1–5 wt-% of an emollient wax. Useful emollient waxes in the present lotions include a $C_{12}$–$C_{18}$ fatty alcohol such as lauryl, cetyl, oleyl and stearyl alcohols or mixtures thereof; and triglycerides of $C_{10}$–$C_{18}$ saturated fatty acids such as the Softisan® series of emollient waxes (Softisan® 100). Preferred fatty alcohols for use in the lotion include cetyl alcohol, commercially available as Crodacol C95-NF (Croda, Inc., New York, N.Y.), and cetearyl alcohol which is a fatty alcohol blend of cetyl and stearyl alcohols and available as Crodacol CS-50 (Croda, Inc., New York, N.Y.).

The emollients may be included in the present lotions as a mix of emollient oil and wax types, as for example, a mix of a fatty alcohol combined with a polyalkylene glycol ether of a fatty alcohol, such as cetearyl alcohol combined with cetereth-20 (a polyethylene glycol ether of cetearyl alcohol), available as Lipowax D (Lipo Chemicals, Inc, Paterson, N.J.). Another useful combination of emollients is a mix of glyceryl monostearate combined with laureth-23, available commercially as Cerasynt 945 (Van Dyk & Co., Belleville, N.J.).

Water. The present lotions will comprise about 70–97 wt-% of a water phase that will include one or more polyhydric alcohol, at least one barrier polymer and a bioactive therapeutic agent. Optionally, the water phase will further include one or more surfactants, preservatives and fragrance. Preferably, the water phase of the lotion includes about 60–70 wt-% water.

Polyhydric Alcohols. The polyhydric alcohols useful in the invention are preferably $C_2$–$C_5$ alkanols substituted with 2–4 hydroxyl groups, such as propylene glycol, glycerol, and sorbitol. The polyhydric alcohols will preferably make up about 1.5–25 wt-% of the water phase of the lotion, and about 0.5–20 wt-% of the total lotion. One especially preferred mixture of polyhydric alcohols is an about 1:1 mixture of propylene glycol and glycerol.

Barrier Polymer. The present lotions further comprise at least one barrier polymer, preferably in an amount that is about 0.5–15 wt-%, more preferably about 1–7 wt-% of the total lotion. The polymer functions to form an occlusive or semi-occlusive film-like barrier on the surface of the skin to prevent evaporative loss of moisture from the skin, and protect the skin against environmental irritants. Preferably, the barrier polymer is soluble in water or a lower alcohol, or ethyl acetate. The barrier polymer may be in an oil phase, a water phase, or a combination thereof.

Useful polymers that may be included in the present lotions include polyvinylpyrrolidone (PVP) (Plasdone K-29/32, GAF Corp., Wayne, N.J.); alkylated vinylpyrrolidone polymers such as butylated polyvinylpyrrolidone (Ganex P-904, GAF Corp.); copolymers of vinylpyrrolidone (VP) such as VP/eicosene copolymer (Ganex V-220, GAF Corp.), PVP/hexadecene copolymer (Ganex V-216, GAF Corp.), PVP/vinyl acetate (PVP/VA) copolymer (PVA/VA E-335, PVA/VA E-535, PVA/VA E-735; GAF Corp.), a PVP/dialkylaminoacrylate copolymer, as for example, PVP/dimethylaminoethylmethacrylate copolymer (Copolymer 937, Copolymer 958, GAF Corp.); and polyquaternary polyvinylpyrrolidones such as polyquaternium-16 (Luviquat FC 370, Luviquat HM 552, BASF). Other useful polymers for use in the lotions include methyl vinyl ether/maleic anhydride copolymers (Gantrez AN-149, Gantrez S-95, GAF Corp.), and polyvinylidene chloride (PVDC) (76 RES M3-153, Union Oil of Calif., San Francisco, Calif.; Saran F-Resin, Dow Corning Corp., Midland, Mich.).

Another class of polymers that may be used are polysaccharide polymers that function not only to provide an occlusive or semi-occlusive barrier on the surface of the skin, but also a timed-release of the therapeutic agent that is included in the present lotions. Polysaccharide polymers such as cellulosics, starches, chitins, chitosans, alginates, carrageenans, agars, agaroses, locust bean gums, konjacs, and modified hydrophobes may be included in the lotion alone or in combination with other polymers. Preferably, a polysaccharide polymer is included in the lotions in an amount of about 0.05–10 wt-%.

Therapeutical Agent. The present lotions include an effective amount of a therapeutic agent, such as a dermatological agent, for the topical treatment of a skin disease or disorder. The therapeutic agent should be chemically compatible with the other ingredients of the composition. Preferably, the lotion includes a therapeutic agent in an amount of about 0.01–10 wt-%.

A wide variety of therapeutic agents may be included in the lotion. Particularly useful in the present lotions are anti-inflammatory agents and topical antipruritics (anti-itch), as for example, non-steroids such as aspirin, camphor, bufexamac, and the like; and steroids such as hydrocortisone, hydrocortisone acetate, hydrocortisone valerate, hydrocortisone butyrate, desonide, triamcinolone acetonide, betamethasone valerate, betamethasone dipropionate, betamethasone benzoate, clobetasol propionate, halcinonide, desoximethasone, amcinonide, fluocinonide, fluandrenolide, alclometasone dipropionate, fluocinolone acetonide, diflorasone diacetate, mometasone furoate, fluorometholone, clocortolone pivalate, triamcinolone acetonide, halcinonide, and the like, and cyclodextrin complexes of these steroids. Preferably, a steroid compound is included in the lotion in an amount of about 0.01–2.5 wt-%.

A dermatological agent may also comprise an antipsoriatic compound such as anthralin (dithranol), coal tar extract, and the like; a keratolytic agent such as salicylic acid, urea, and the like; a local anaesthetic agent such as lidocaine, benzocaine, and the like; an anti-acne agent such as benzoyl peroxide, vitamin A derivatives, and the like; and a wart removing agent such as salicylic acid, lactic acid, and the like; and other like agents.

Penetrating Enhancing Agent. The lotions may also include an effective amount of a penetration enhancing agent, or pharmacologically inert substance that is capable of enhancing the penetration rate of a therapeutic agent through the skin. Preferably, the penetration enhancing agent will increase the flux rate of a therapeutic agent through the skin by altering the thermodynamic activity of a penetrant or a co-solvent incorporated into the lotion, or by affecting the partition coefficient between the therapeutic agent and the skin to promote release of the therapeutic agent from the lotion into the skin, and the like.

Penetration enhancers that are useful in the present lotions include, but are not limited to, dimethyl sulfoxide, N,N-dimethyl acetamide, 2-pyrrolidone, 1-methyl-2-pyrrolidone, Carbitol solvent (Union Carbide), propylene carbonate, 1,5-dimethyl-2-pyrrolidone, 2-pyrrolidone-5-carboxylic acid, and the like. Preferably, the lotion includes a penetration enhancing agent in an amount of about 0.01–20 wt-%.

ADJUVANTS

Surfactants. The lotions may optionally include one or more surfactants to stabilize the oil-in-water emulsion.

Preferably, the lotions further include a minor but effective amount of an ionic surfactant, preferably about 0.1–10 wt-%, as for example, ethoxylated fatty alcohol carboxylates such as sodium ceteth-13-carboxylate (Sandopan KST, Sandoz, Inc., East Hanover, N.J.), and sodium laureth-13-carboxylate (Sandopan LS-24, Sandoz, Inc., East Hanover, N.J.).

To achieve optimal homogeneity of the oil-in-water emulsions of the present invention, it is desirable to include an effective amount of one or more amphoteric surfactants in the water phase of the lotions, for example, about 1–10 wt-% of the total weight of the water phase, more preferably about 1–6 wt-%, and about 1–3 wt-% of the total weight of the lotion, more preferably about 1–5 wt-%. Preferred amphoteric surfactants are the amine oxides, such as the $C_{10}$–$C_{20}$-alkyl-di(lower)alkyl-amine oxides or the $C_{10}$–$C_{20}$-alklylamido($C_2$–$C_5$)alkyl-di(lower)-amine oxides. Especially preferred members of this class include lauryl (dimethyl)amine oxide (Standamax LAO-30, Henkel Corp., Ambler, Pa.), myristyl(dimethyl)amine oxide (Bio-Surf® PBC-460, Biolab, Decatur, Ga.), stearyl(dimethyl)amine oxide (Schercamox DMS, Scher Chemicals, Inc., Clifton, N.J.), coco(bis-hydroxyethyl)amine oxide (Schercamox CMS), tallow(bis-hydroxyethyl)amine oxide, and cocoamidopropyl(dimethyl)amine oxide (Standamax LAO-30, Henkel Corp., Ambler, Pa.).

Buffer/Acidifying Agent. An effective amount of a buffer/acidifying agent may optionally be included in the water phase of the lotion, as for example, an organic acid such as citric acid, a salt of an organic acid such as sodium citrate, $H_3PO_4$ plus buffer, and the like. Preferably, the lotion contains about 0.01–0.9 wt-% of citric acid.

Antimicrobial Agents. Minor but effective amounts of one or more compatible antimicrobial agent may also be included in the present lotions to control fungal and bacterial growth both during storage of the composition before use, and between applications. Preferably, one or more such agents will be included in both the oil phase and the water phase. Preferably, antimicrobial agents will make up about 0.025–1 wt-% of the total lotion.

The antimicrobial agents included in the lotion should not induce undesirable interactions or chemical reactions between the major components of the lotions. Antimicrobial agents that are useful in the present lotions include chlorhexidine gluconate, glutaral, halazone, hexachlorophene, nitrofurazone, nitromersol, povidone-iodine, thimerosal, $C_1$–$C_5$-parabens, clofurcaban, chlorophene, polosamer-iodine, phenolics, mefanide acetate, aminacrine hydrochloride, oxychlorosene, metabromsalene, merbromine, dibromsalan and the like. Preferred cationic germicidal agents include the salts of substituted amines.

An especially preferred class of preservatives is the parabens family, the $C_1$–$C_4$ lower alkyl- or benzyl-esters of p-hydroxy-benzoic acids which also act to stabilize the emulsions. Preferred parabens for inclusion in the present lotions are methyl paraben, butyl paraben and propyl paraben, available commercially, respectively, as Unisept M, Unisept B and Unisept P (Universal Preserv-a-Chem, Inc. (UPI), New York, N.Y.), preferably, included in the lotion in an amount of about 0.2–1 wt-%.

Another preferred preservative for use in the lotions of the present invention is an aqueous solution of 5-chloro-2-methyl-4-isothiazolin-3-one which is commercially available as a 10–11% aqueous solution in combination with 3–4% 2-methyl-1-isothiazoline-3-one under the trade name Kathon®CG concentrate from Rohm and Haas Co., Philadelphia, Pa.

Fragrance. Optionally, the lotions may also include a minor, i.e., 0.01–5 wt-%, but effective amount of fragrance for cosmetic purposes. The fragrances may be any of the commercially available perfumes which are chemically-compatible with the other emulsion ingredients. Representative, suitable fragrances are disclosed by S. Arctander, in *Perfume and Flavor Materials of Natural Origin*, Det Hoffensbergske Establissement, Denmark (1960), the disclosure of which is incorporated by reference herein. Useful fragrances will include, for instance about 0.025–2 wt-%, preferably about 0.05–1.5 wt-% of floral oils such as rose oil, lilac, jasmine, wisteria, apple blossom, or compounds bouquets such as spice, aldehydic, woody, oriental, and the like.

Formulations. Preferred lotions useful in the present invention may be formulated so as to contain about 50–90 wt-% water, about 0.5–20 wt-% emollients, about 0.5–20 wt-% polyhydric alcohol, about 0.5–15 wt-% barrier polymer, and about 0.01–10 wt-% of a therapeutical agent, preferably about 0.01–2.5 wt-% steroid. Preferably, the lotion will further include about 1–10 wt-% surfactant, preferably about 1–3 wt-% of an amphoteric surfactant and about 0.5–5 wt-% of an ionic surfactant, and about 0.025–1 wt-% of an antimicrobial preservative.

In a preferred embodiment, the present lotions comprise:
  (a) about 60–70 wt-% water;
  (b) about 0.5–20 wt-% emollients, comprising:
    (i) about 0.75–3 wt-% of a phytosterol;
    (ii) about 1–5 wt-% of a fatty alcohol benzoate;
    (iii) about 1–5 wt-% of a 1:1 mix of a fatty acid-polyol ester and a polyoxyalkylene derivative of a fatty alcohol;
    (iv) about 1–5 wt-% mineral oil; and
    (v) about 0.1–5 wt-% of a $C_{12}$–$C_{18}$ fatty alcohol;
  (c) about 1–7 wt-% of a barrier polymer;

(d) about 1–9 wt-% of a polyhydric alcohol;

(e) minor but effective amounts of a therapeutical agent, preferably a dermatological agent such as asteroid.

A preferred lotion will further comprise about 0.01–20 wt-% of a penetration enhancing agent, and minor but effective amounts of surfactant, preferably an amphoteric and an ionic surfactant, an antimicrobial agent, preferably one or more of a paraben compound, and/or fragrance.

PREPARATION

The lotions of the present invention are generally prepared by melting together the emollients and a part of the preservatives with stirring or shaking at temperatures in the range of about 75°–85° C. in order to prepare the oil phase of the lotion. The hot oil phase is then added with vigorous agitation to the aqueous phase which has been separately prepared by dissolving the polyhydric alcohol, a part of the preservatives, and the amphoteric surfactant/citric acid solution, i.e., the alkyl dimethyl amine oxide, in water and heating the resultant solution to the same temperature as the oil phase. After a brief period of stirring, the resultant 65°–75° C. pre-emulsion is stabilized by the subsurface addition Of the nonionic surfactant which has been separately dissolved in a small portion of water and heated to about 50°–60° C. The emulsion is stirred and cooled to about 40°–50° C., at which point the steroid which has been separately dissolved in a small amount of aqueous alcohol at about 35°–45° C., is slowly added. The mixture is stirred and cooled to below 40° C.

The lotions of the present invention may be incorporated into an absorbent sheet, such as a fibrous or cellular flexible material that can retain sufficient amounts of the lotion to effectively apply the lotion to the surface of the skin without leaking or bleeding during storage of the sheet or administration of the lotion to the skin. Absorbent sheets that may be used for applying the lotion include those describe, for example, in Smith et al., U.S. Pat. Nos. 4,690,821 and 4,559,157.

The lotions of the present invention may be used for treating a skin disorder or disease, such as psoriasis, eczema, atopic dermatitis, alopecia areata, warts, keratoses, acne, and the like. The lotion is spread over the diseased or irritated portion of the skin and allowed to dry to a film on the surface of the skin. The composition is then maintained on the skin surface for a predetermined period of time that is effective to deliver the therapeutic agent to the skin to provide the desired treatment of the skin disorder. The occlusive/semi-occlusive nature of the film on the surface of the skin retains moisture from the skin to promote delivery of the therapeutic agent to the skin surface.

The invention will be further described by reference to the following detailed examples. These examples are not meant to limit the scope of the invention that has been set forth in the foregoing description, and it should be understood that many variations and modifications may be made while remaining within the spirit and scope of the invention.

EXAMPLE I (JS-4-26)

Moisturizing Occlusive Lotion for Treatment of Psoriasis containing 0.05% Betamethasone Dipropionate A composition was prepared containing betamethasone dipropionate, asteroid useful in treating psoriasis.

The following ingredients were combined according to the protocol described below.

| INGREDIENTS | wt % |
|---|---|
| OIL PHASE | |
| Cerasynt 945 (glyceryl stearate and laureth-23) | 3.5 |
| Crodacol C95-NF (cetyl alcohol) | 0.5 |
| Lipowax D (cetearyl alcohol and cetereth-20) | 1.5 |
| Mineral Oil Light | 4.0 |
| Finsolv TN ($C_{12}$–$C_{15}$ alcohols benzoate) | 3.0 |
| Generol 122E-16 (PEG-16 Soya Sterol) | 1.0 |
| AQUEOUS PHASE | |
| Propylene glycol | 5.0 |
| Glycerin (96%) | 4.0 |
| Standamax LAO-30 (lauramine oxide) | 3.0 |
| Citric acid (10%) | 2.0 |
| Water | 61.5 |
| POLYMER | |
| VP/VA Copolymer (PVP/VA E-535) | 5.0 |
| NONIONIC SURFACTANT | |
| Sandopan KST (sodium ceteth-13-carboxylate) | 0.3 |
| Sandopan LS-24 (sodium laureth-13-carboxylate) | 0.2 |
| STEROID SOLUTION | |
| Isopropyl alcohol (USP) | 5.0 |
| Betamethasone Dipropionate | 0.06 |
| PRESERVATIVES | |
| Propyl Paraben | 0.1 |
| Butyl Paraben | 0.05 |
| Methyl Paraben | 0.3 |
| | 100.0 |

The PVP/VA E-535 polymer was added with agitation to a vessel that contained 92% of the total (61.5 wt-%) distilled water and was placed in heated water bath (76° C.). After the polymer was fully dispersed into solution, the propylene glycol and glycerin were added to the aqueous mixture with continuous mixing.

In a separate vessel, the 10% citric acid was stirred into the Standamax LAO-30 surfactant, and the solution was added to the heating aqueous mixture. The powdered methyl paraben was then added to the aqueous mixture which was stirred until the preservative was dissolved. The mixture was continuously and rapidly agitated and heated to 76° C. in the water bath.

In a separate vessel, the oil phase was prepared by combining the Cerasynt 945, Crodacol C-95 NF, Lipowax D, mineral oil, Finsolv TN, Generol 122 E-16 and the two other preservatives, propyl paraben and butyl paraben. The oil phase mixture was heated to 78° C. with agitation until all the components were melted and a clear, hot, uniform mixture was achieved.

The oil phase at 78° C. was then added to the aqueous phase of the lotion by means of a subsurface-addition technique with rapid agitation of the mixture. The addition rate of the oil phase into the aqueous phase was at 1.092 grams of the oil phase per second. The total time for the addition was 2.5 minutes. The resulting emulsion that was formed had a temperature of 76° C. Agitation of the oil-in-water emulsion was continued, and the temperature of the emulsion was maintained at 76° C. in the water bath.

In a separate vessel, the nonionic surfactant solution, Sandopan KST and Sandopan LS-24, was dissolved in the remaining water (8%). The resulting solution was heated to 60° C. At 5 minutes following the addition of the oil phase into the aqueous phase, the surfactant solution was slowly added to the oil-in-water emulsion.

In the water bath, the emulsion was gradually cooled down with continuous agitation to 40° C. In a separate vessel, the powdered steroid was dissolved in isopropanol at 40° C., and then slowly added with continuous agitation to the cooled (40° C.) emulsion. The lotion was then cooled to 26° C., and bottled. The pH of the lotion was 4.5.

EXAMPLE II (JS-4-27)

Moisturizing Occlusive Lotion for Treatment of Atopic Dermatitis containing 0.05% fluocinonide A lotion was prepared containing the corticosteroid, fluocinonide, which is used for treatment of atopic dermatitis.

The ingredients listed in Example I were combined, except that 0.05% of fluocinonide was substituted for the betamethasone dipropionate. Also, the steroid component was added directly into the aqueous phase as part of the initial emulsification step.

A 92% portion of the total distilled water was placed into a vessel equipped with a suitable agitator and water bath. The PVP/VA E-535 copolymer solution was added to the aqueous phase with stirring, and the mixture was heated to 76° C. in the water bath. The propylene glycol and glycerin were added with continuous mixing. In a separate vessel, the Standamax LAO-30 surfactant was acidified with 10% citric acid solution, and the surfactant/citric acid solution was added to the heating aqueous phase.

In a separate vessel, the fluocinonide was dissolved in isopropanol by heating the mixture to 65° C. The steroid/alcohol solution was slowly added to the aqueous phase while heating the mixture to 76° C. in the water bath. The resulting aqueous phase mixture was a clear, hot solution. The powdered methyl paraben was then added to the aqueous phase with continuous agitation while the mixture was maintained in the water bath at 76° C.

The oil phase was prepared as described in Example 1, by combining the Cerasynt 945, Crodacol C95-NF, Lipowax D, mineral oil, Finsolv TN, Generol 122 E-16 and the parabens in a separate vessel. The oil phase mixture was heated to 78° C., and then added into the water phase (76° C.) by means of subsurface addition with rapid agitation. The addition time of the oil phase into the aqueous phase was 2.5–3.0 minutes. The oil-in-water emulsion was maintained in the water bath temperature at 76° C. under continuous agitation.

The nonionic surfactant solution (Sandopan KST and Sandopan LS-24 in water; 60° C.) was prepared in a separate vessel. After the oil-in-water emulsion had been stirred for 5 minutes, the surfactant solution was added to the emulsion. The addition time was 25 seconds. The lotion was then cooled gradually over a period of 2 ½ hours. The final temperature of the lotion was 26° C.

EXAMPLE III (JS-4-97)

Occlusive Polymer Steroid Lotion Base containing 0.05% Betamethasone Dipropionate A composition was prepared containing betamethasone dipropionate.

The ingredients listed in Example I were combined according to the described protocol, except that the copolymer was PVP/VA I-735. Also, the steroid component was dissolved in propylene glycol instead of isopropyl alcohol, at 70° C., and added into the aqueous phase at 75° C.

EXAMPLE IV (JS-4-99)

Occlusive Polymer Steroid Lotion Base containing 0.05% Betamethasone Dipropionate and Penetration Enhancing Agent (m-pyrrol)

A composition was prepared containing betamethasone dipropionate with the addition of a penetration enhancing agent, m-pyrrol.

The ingredients listed in Example I were combined according to the described protocol, except that the copolymer was PVP/VA I-535, and the total water component was 65.74 wt-%. Also, the steroid component (0.06 wt-%) was dissolved in propylene glycol (5 wt-%) instead of isopropyl alcohol, and m-pyrrol (0.75 wt-%) at 75° C., and added into the aqueous phase at 75° C.

EXAMPLE V (JS-4-101)

Occlusive Polymer Steroid Lotion Base containing 0.05% Betamethasone Dipropionate and Penetration Enhancing Agent (propylene carbonate)

A composition was prepared containing betamethasone dipropionate with the addition of a penetration enhancing agent, propylene carbonate.

The ingredients according to Example I were combined according to the described protocol, except that the copolymer was PVP/VA I-535, and the total water component was 65.74 wt-%. Also, the steroid component (0.06 wt-%) was dissolved in propylene glycol (5 wt-%) and propylene carbonate (0.75 wt-%) at 75° C., and added into the aqueous phase at 75° C.

EXAMPLE VI (JS-4-103)

Occlusive Polymer Steroid Lotion Base containing 0.05% Betamethasone Dipropionate and Penetration Enhancing Agent (carbitol solvent)

A composition was prepared containing betamethasone dipropionate with the addition of a penetration enhancing agent, carbitol solvent.

The ingredients according to Example I were combined according to the described protocol, except that the copolymer was PVP/VA I-535, and the total water component was 65.74 wt-%. Also, the steroid component (0.06 wt-%) was dissolved in propylene glycol (5 wt-%) and carbitol solvent (0.75 wt-%) at 75° C., and added into the aqueous phase at 75° C.

EXAMPLE VII (JS-4-105)

Occlusive Polymer Steroid Lotion Base without alcohol containing 0.05% Betamethasone Dipropionate and Penetration Enhancing Agent (triglyceride)

A composition was prepared containing betamethasone dipropionate with the addition of a penetration enhancing agent, triglyceride.

The ingredients according to Example I were combined according to the described protocol, except that the copolymer was PVP/VA I-735, and Myritol 318 (carprylic/capric triglyceride; Henkel Corp., Ambler, Pa.) replaced the Finsolv TN to improve penetration of the steroid into the skin. Also, the steroid component was dissolved in propylene glycol instead of isopropyl alcohol, at 70° C., and added into the aqueous phase at 75° C.

EXAMPLE VIII (JS-4-109)

Occlusive Polymer Steroid Lotion Base containing 0.05% Betamethasone Dipropionate with steroid added into the oil phase A composition was prepared containing betamethasone dipropionate.

The ingredients according to Example I were combined according to the described protocol, except that the copolymer was PVP/VA I-735.

Also, the steroid component was added into the oil phase instead of the aqueous phase, at 75° C., as follows. The flask was charged with Finsolv TN, and the steroid mixed in and heated to 75° C. The mineral oil component and the Cerasynt 945 were then added into the mixture, followed by the Crodacol C95-NF and Lipowax D, the General 122E-16, and finally the parabens.

EXAMPLE IX (JS-4-107)

Occlusive Polymer Steroid Lotion Base without alcohol containing 0.05% Betamethasone Dipropionate with pH adjustment with $H_3PO_4$ A composition was prepared containing betamethasone dipropionate, with the addition of phosphoric acid to adjust the pH of the mixture.

The ingredients according to Example I were combined according to the described protocol, except that the total amount of water was 68.7 wt-%, and the total amount of copolymer (PVP/VA I-535) was 2.5 wt-%. Also, the steroid component was dissolved in propylene glycol instead of isopropyl alcohol, at 70° C., and added into the aqueous phase at 75° C.

To adjust the pH of the mixture, 10% phosphoric acid (2.2 wt-%) and sodium phosphate monobasic (0.1 wt-%) were added to the aqueous phase.

What is claimed is:

1. A film forming lotion for topical administration, comprising an oil-in-water emulsion consisting essentially of:
   (i) an aqueous phase comprising, by total weight of lotion:
      (A) about 60–90 wt-% water;
      (B) about 0.5–20 wt-% polyhydric alcohol; and
      (C) about 1–15 wt-% of a water-soluble barrier polymer selected from the group consisting of polyvinylpyrrolidone, an alkylated vinylpyrrolidone, a copolymer of vinylpyrrolidone, a polyquaternary vinylpyrrolidone, and combination thereof;
   (ii) an oil phase comprising, by total weight of lotion:
      (D) about 0.5–20 wt-% emollient, said emollient comprising
         (a) about 0.75–3% of a phytosterol;
         (b) about 1–5% of a fatty alcohol benzoate;
         (c) about 1–5% of a mixture of a fatty acid-polyol ester and a polyoxyalkylene derivative of a fatty alcohol;
         (d) about 1–5% mineral oil; and
         (e) about 0.1–5 % of a $C_{12}$–$C_{18}$ fatty alcohol, and
   (iii) about 0.01–10 wt-% of a therapeutical agent; wherein upon application to the skin, the lotion forms an occlusive or semi-occlusive water soluble polymeric barrier film that retains the therapeutic agent in intimate contact with the surface of the skin.

2. The lotion of claim 1 comprising 1–7% of a polyhydric alcohol.

* * * * *